United States Patent
Rosa

(10) Patent No.: US 12,029,512 B2
(45) Date of Patent: Jul. 9, 2024

(54) INCREASED USABLE INSTRUMENT LIFE IN TELESURGICAL SYSTEMS

(71) Applicant: Intuitive Surgical Operations, Inc., Sunnyvale, CA (US)

(72) Inventor: David J. Rosa, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 734 days.

(21) Appl. No.: 16/932,420

(22) Filed: Jul. 17, 2020

(65) Prior Publication Data

US 2020/0345437 A1 Nov. 5, 2020

Related U.S. Application Data

(63) Continuation of application No. 16/637,869, filed as application No. PCT/US2018/044060 on Jul. 27, 2018, now Pat. No. 11,617,628.

(Continued)

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/25* (2016.02); *A61B 34/37* (2016.02); *A61B 34/71* (2016.02);
(Continued)

(58) Field of Classification Search
CPC ......... A61B 34/35; A61B 34/25; A61B 34/37; A61B 34/71; A61B 90/03; A61B 90/08;
(Continued)

(56) References Cited

U.S. PATENT DOCUMENTS

| | | |
|---|---|---|
| 5,279,309 A | 1/1994 | Taylor et al. |
| 5,400,267 A | 3/1995 | Denen et al. |

(Continued)

FOREIGN PATENT DOCUMENTS

| | | |
|---|---|---|
| CN | 102188270 A | 9/2011 |
| CN | 103608150 A | 2/2014 |

(Continued)

OTHER PUBLICATIONS

International Search Report and Written Opinion for Application No. PCT/US2018/044060, dated Feb. 20, 2019, 18 pages.

(Continued)

*Primary Examiner* — Aaron F Roane
(74) *Attorney, Agent, or Firm* — Haynes and Boone, LLP.

(57) ABSTRACT

A telesurgical system may comprise a teleoperated manipulator and a control system to execute instructions to perform operations. The operations may comprise determining a remaining usable life value of a surgical instrument. The surgical instrument may comprise a distal end component and an actuation component coupled to move the distal end component when driven by the teleoperated manipulator. The operations may also comprise monitoring an amount of use of the actuation component during a use of the surgical instrument. Monitoring the amount of use of the actuation component comprises determining the amount of use of the actuation component based on a force or torque on the actuation component. The operations may also comprise updating the remaining usable life value to an updated usable life value of the surgical instrument based at least on the amount of use of the actuation component during the use of the surgical instrument.

28 Claims, 3 Drawing Sheets

Related U.S. Application Data

(60) Provisional application No. 62/543,726, filed on Aug. 10, 2017.

(51) Int. Cl.
  *A61B 34/37*  (2016.01)
  *A61B 90/00*  (2016.01)
  *A61B 34/30*  (2016.01)

(52) U.S. Cl.
  CPC .............. *A61B 90/03* (2016.02); *A61B 90/08* (2016.02); *A61B 2034/301* (2016.02); *A61B 2034/302* (2016.02); *A61B 2034/303* (2016.02); *A61B 2090/0803* (2016.02)

(58) Field of Classification Search
  CPC ........ A61B 2034/301; A61B 2034/302; A61B 2034/303; A61B 2090/0803
  USPC ......................................................... 606/130
  See application file for complete search history.

(56) References Cited

U.S. PATENT DOCUMENTS

| | | |
|---|---|---|
| 6,424,885 B1 | 7/2002 | Niemeyer et al. |
| 8,608,773 B2 | 12/2013 | Tierney et al. |
| 9,266,239 B2 | 2/2016 | Miller |
| 11,617,628 B2 | 4/2023 | Rosa |
| 11,747,895 B2 * | 9/2023 | Zhao ....................... G06F 3/013 715/771 |
| 2003/0093103 A1 | 5/2003 | Malackowski et al. |
| 2007/0156285 A1 | 7/2007 | Sillman et al. |
| 2010/0063601 A1 | 3/2010 | Sankai et al. |
| 2010/0274087 A1 | 10/2010 | Diolaiti et al. |
| 2011/0118778 A1 | 5/2011 | Burbank |
| 2013/0012959 A1 | 1/2013 | Jinno |
| 2013/0172908 A1 | 7/2013 | Sang et al. |
| 2014/0121834 A1 | 5/2014 | Ogawa et al. |
| 2015/0313676 A1 | 11/2015 | Deodhar |
| 2016/0135909 A1 | 5/2016 | Ogawa et al. |
| 2016/0361048 A1 | 12/2016 | Alden et al. |
| 2017/0212995 A1 | 7/2017 | Ingmanson |
| 2017/0215975 A1 | 8/2017 | Nowlin et al. |
| 2017/0333073 A1 | 11/2017 | Faller et al. |
| 2018/0036090 A1 | 2/2018 | Hasegawa et al. |
| 2018/0296290 A1 | 10/2018 | Namiki et al. |
| 2018/0368821 A1 * | 12/2018 | Shelton, IV ..... A61B 17/00234 |
| 2021/0369377 A1 | 12/2021 | Rosa |

FOREIGN PATENT DOCUMENTS

| | | |
|---|---|---|
| CN | 105011979 A | 11/2015 |
| CN | 105407827 A | 3/2016 |
| CN | 106456172 A | 2/2017 |
| EP | 2923661 A2 | 9/2015 |
| JP | 2004537367 A | 12/2004 |
| JP | 2007316860 A | 12/2007 |
| JP | 2012115553 A | 6/2012 |
| JP | 2012161590 A | 8/2012 |
| JP | 2013022651 A | 2/2013 |
| JP | 2015024036 A | 2/2015 |
| JP | 2016117148 A | 6/2016 |
| JP | 6157786 B1 | 7/2017 |
| WO | WO-2011060311 A2 | 5/2011 |
| WO | WO-2011114924 A1 | 9/2011 |
| WO | WO-2013012018 A1 | 1/2013 |
| WO | WO-2015142780 A1 | 9/2015 |
| WO | WO-2016077419 A1 | 5/2016 |
| WO | WO-2017115425 A1 | 7/2017 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action for Chinese Application No. CN20188060160, dated Sep. 14, 2022, 21 pages.

Supplementary European Search Report for Application No. EP18844930.0 dated Nov. 9, 2020, 08 pages.

* cited by examiner

INCREASED USABLE INSTRUMENT LIFE IN TELESURGICAL SYSTEMS

CROSS-REFERENCE TO RELATED APPLICATION

This application is a continuation of and claims priority to U.S. patent application Ser. No. 16/637,869, filed on Feb. 10, 2020, which is a U.S. National Stage Application under U.S.C. § 371 and claims the benefit of International Patent Application number PCT/US2018/044060, filed on Jul. 27, 2018, which claims priority to U.S. Provisional Patent Application No. 62/543,726, filed on Aug. 10, 2017, the entire contents which are hereby incorporated by reference.

TECHNICAL FIELD

Inventive aspects are associated with operating modes for teleoperated surgical systems and instruments.

BACKGROUND

Minimally invasive surgical techniques may reduce the amount of damage to tissue during diagnostic or surgical procedures, thereby reducing patient recovery time, discomfort, and unhealthy side effects. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for surgical instruments. Other forms of minimally invasive surgery include thoracoscopy, arthroscopy, and similar "keyhole" surgeries that used to carry out surgical procedures in the abdomen, thorax, throat, rectum, joints, etc.

Teleoperated surgical systems that use computer assistance are known. These surgical systems are used for both minimally invasive surgeries, and also for "open" surgeries in which an incision is made sufficiently large to allow a surgeon to access a surgical site. Examples of minimally invasive and open surgeries include the surgeries listed above, as well as surgeries such as neurosurgery, joint replacement surgery, vascular surgery, and the like, using both rigid- and flexible-shaft teleoperated surgical instruments. An example of a teleoperated surgical system is the da Vinci Xi® Surgical System (Model IS4000), commercialized by Intuitive Surgical, Inc., Sunnyvale, California Other examples include the Sensei® and Magellan™ Systems commercialized by Hansen Medical (Auris Surgical Robotics Inc.), the RIO™ System commercialized by Mako Surgical (Stryker Corporation), and the Flex® System commercialized by Medrobotics Corporation.

Teleoperated surgical systems may use interchangeable surgical instruments that are driven by robotic manipulator technology. Some of these instruments are intended for only a single use, or for use during only a single surgical procedure. These instruments are treated as disposable because they are not used again. Some of these single-use instruments are expensive, and consequently the cost of a surgical procedure increases. Other instrument types are designed for multiple uses, and these multiple-use instruments are typically cleaned and sterilized between surgical procedures. An advantage of multiple-use instruments is that the instrument cost per surgical procedure is reduced. But, mechanical limitations such as cable wear limit the number of times these multiple-use instruments can be used. Thus an increase in the number of times a multiple-use instrument can be used will further reduce instrument cost per surgical procedure.

SUMMARY

In one aspect, a surgical system includes a teleoperated manipulator and a control system. An instrument is coupled to the manipulator, and the instrument includes a movable mechanical component. The control system operates the surgical system in a first operating mode in which the control system drives the movable mechanical component within a first range of an operating parameter, such as a full range of motion of the mechanical component. And, the control system also operates the surgical system in a second operating mode in which the control system drives the movable mechanical component with a second range of the operating parameter that is more limited than the first range, such as less than the full range of motion of the mechanical component. Other operating parameters include velocity, acceleration, and mechanical load. And additional operating modes and parameter ranges may optionally be used.

A surgeon may select one or more operating modes as clinically required.

The usable life of the instrument is reduced based on the extent of operating in the first operating mode and in the second operating mode. Alternately, the usable life of the instrument is reduced based on the extent of operating in the first operating parameter range and in the second operating parameter range. Operating within the second, more limited parameter range results in relatively less mechanical wear on the component. The amount of usable life remaining on the instrument is reduced by one amount corresponding to operating in the first operating mode or within the first parameter range, and the amount of usable life remaining on the instrument is reduced by a second amount, less than the first amount, corresponding to operating in the first operating mode or within the first parameter range. As a result, an instrument's usable life is increased, and overall cost per surgical procedure is reduced.

Additional aspects of limiting mechanical component operation to generate a corresponding increase in usable instrument life are presented.

DETAILED DESCRIPTION

Figure 1:
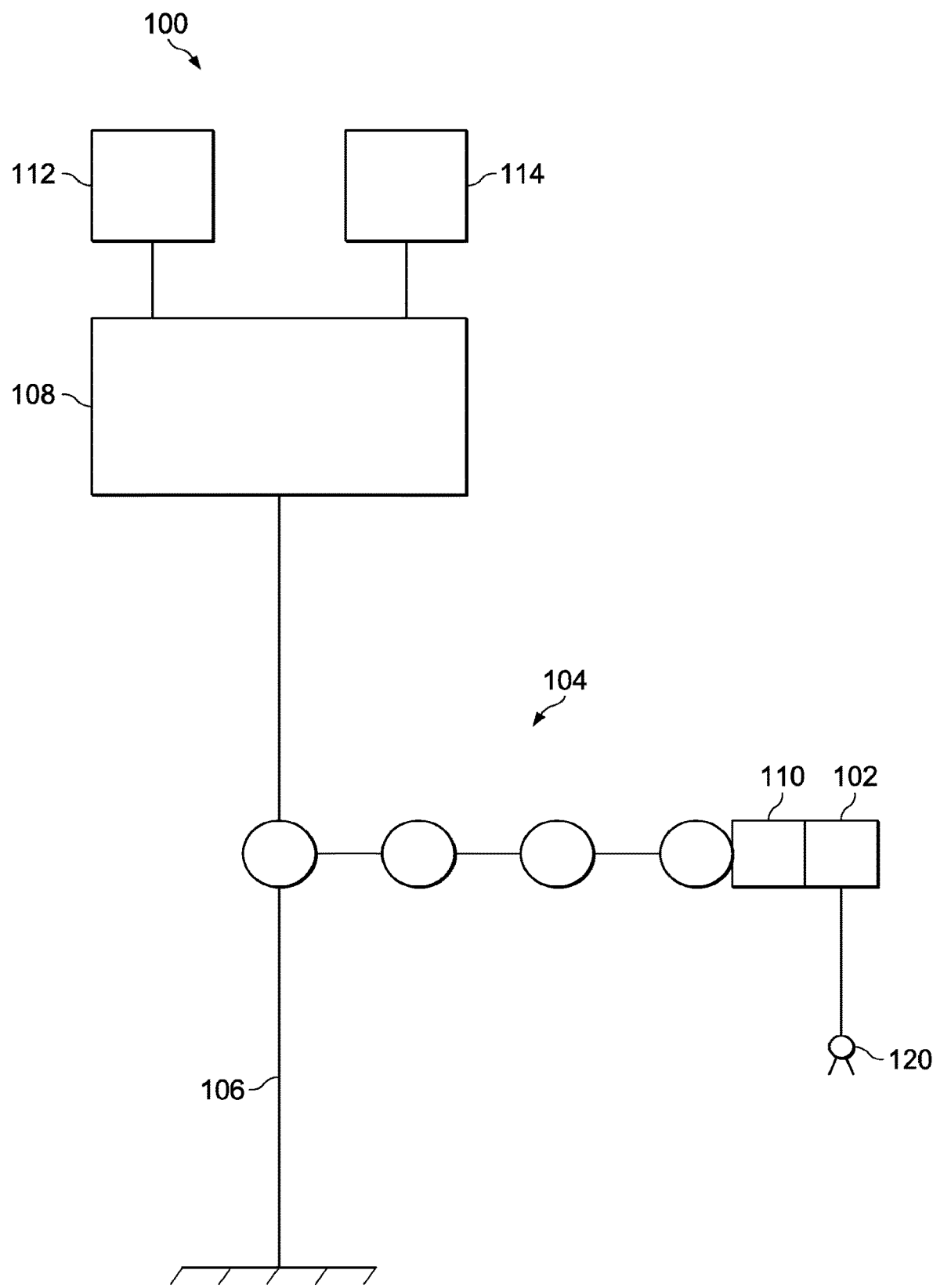
FIG. 1 is a schematic view of a telesurgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. The singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other like, similar, or different features, steps, operations, elements, components, and/or groups.

It should be understood that although this description is made to be sufficiently clear, concise, and exact, scrupulous and exhaustive linguistic precision is not always possible or desirable. For example, considering a video signal, a skilled reader will understand that an oscilloscope described as displaying the signal does not display the signal itself but a representation of the signal, and that a video monitor described as displaying the signal does not display the signal itself but video information the signal carries.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

Aspects of the invention are described primarily in terms of an implementation using a da Vinci® Surgical System, commercialized by Intuitive Surgical, Inc. of Sunnyvale, California Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted and hybrid combinations of manual and computer-assisted embodiments and implementations. Implementations on da Vinci® Surgical Systems (e.g., the Model IS4200, the Model IS4000, the Model IS3000, the Model IS2000, the Model IS1200) are merely exemplary and are not to be considered as limiting the scope of the inventive aspects disclosed herein. As applicable, inventive aspects may be embodied and implemented in both relatively smaller, hand-held, hand-operated devices and relatively larger systems that have additional mechanical support.

Teleoperated surgical systems that operate at least in part with computer assistance ("telesurgical systems") include both mechanically-grounded and hand-held devices. Such telesurgical systems typically include one or more surgical instruments for therapeutic, diagnostic, or imaging use. In hand-held telesurgical systems, such as surgical staplers and bone tools, the instrument and hand-held portion are typically combined. In mechanically-grounded systems, the instrument is typically mechanically supported with reference to a mechanical ground.

This description concentrates on mechanically-grounded telesurgical systems, although aspects apply to hand-held telesurgical systems as appropriate. An example of a mechanically-grounded telesurgical system is the da Vinci® Surgical System. Persons of skill in the art will be familiar with various telesurgical system architectures, such as ones described in U.S. Pat. No. 6,246,200 B1 (filed Aug. 3, 1999), U.S. Pat. No. 6,331,181 B1 (filed Oct. 15, 1999), and U.S. Pat. No. 6,788,018 B1 (filed Dec. 20, 2001).

FIG. 1 is a schematic view of a telesurgical system 100 and a surgical instrument 102 associated with the telesurgical system. System 100 and instrument 102 are illustrative of various telesurgical system configurations. As shown, major components of the telesurgical system include a teleoperated manipulator 104, a base unit 106, and a computer control system 108. These major components and their associated functions may be configured as a single unit, or they may be distributed among two, three, or more separate and interconnected units. For example, the da Vinci Xi® Surgical System includes a teleoperated manipulator system that is located next to a patient (a "patient-side unit"), a surgeon control unit located remote from the patient-side unit, and an auxiliary equipment unit.

Manipulator 104 includes a series of links interconnected by joints and extends from base unit 106 to a distal instrument drive interface 110, on which instrument 102 is mounted. As shown, manipulator 104 is illustrative of various teleoperated manipulator configurations that move instrument 102 as a whole, move one or more individual components of instrument 102 while keeping the main portion of instrument 102 stationary, or both. Manipulator 104 operates under the control of a surgeon, who inputs motion control and instrument function operating commands to control system 108, which in turn commands manipulator 104 to execute the corresponding movement or function. In optional aspects, however, control system 108 may autonomously command certain manipulator 104 movements or instrument 102 functions associated with carrying out a medical procedure.

As shown, base unit 106 is mechanically grounded, although it may optionally be ungrounded, for example in hand-held embodiments. Base unit 106 is illustrative of various separate or combined configurations of one or more patient-side units (e.g., a single unit with two or more manipulators, two or more units each with a single manipulator, etc.), a surgeon control unit, and one or more auxiliary equipment units.

Computer control system 108 may be centralized or distributed within the telesurgical system. And as discussed below, aspects of computer control system 108 and instrument data associated with computer control system 108 may be remote from the telesurgical system, for example at a location in a network to which the telesurgical system is coupled. Computer control systems are known, and they generally include a logic unit and a memory system that stores instructions to be carried out by the logic unit and data acted on by the logic unit. U.S. Pat. No. 6,424,885 B1 (filed Aug. 13, 1999), which is incorporated herein by reference, is an example of a computer control system for a telesurgical system.

Computer control system 108 receives a user's surgical instrument movement commands via master input 112 and correspondingly controls manipulator 104 so that instrument 102 motions are slaved to master input 112 motions. Master input 112 may optionally have one or more additional control inputs that control instrument 102 functions via control system 108, such as electrosurgical energy application, surgical staple application, etc. As shown, computer control unit 108 also receives a user's instrument operating mode commands via operating mode input 114. Aspects of these operating modes will be discussed in detail. Operating mode input 114 may be combined with master input 112 or it may be separately located. For example, operating mode input 114 may be a switch on the master input or on a surgeon control unit touch pad or similar input device.

Figure 2:
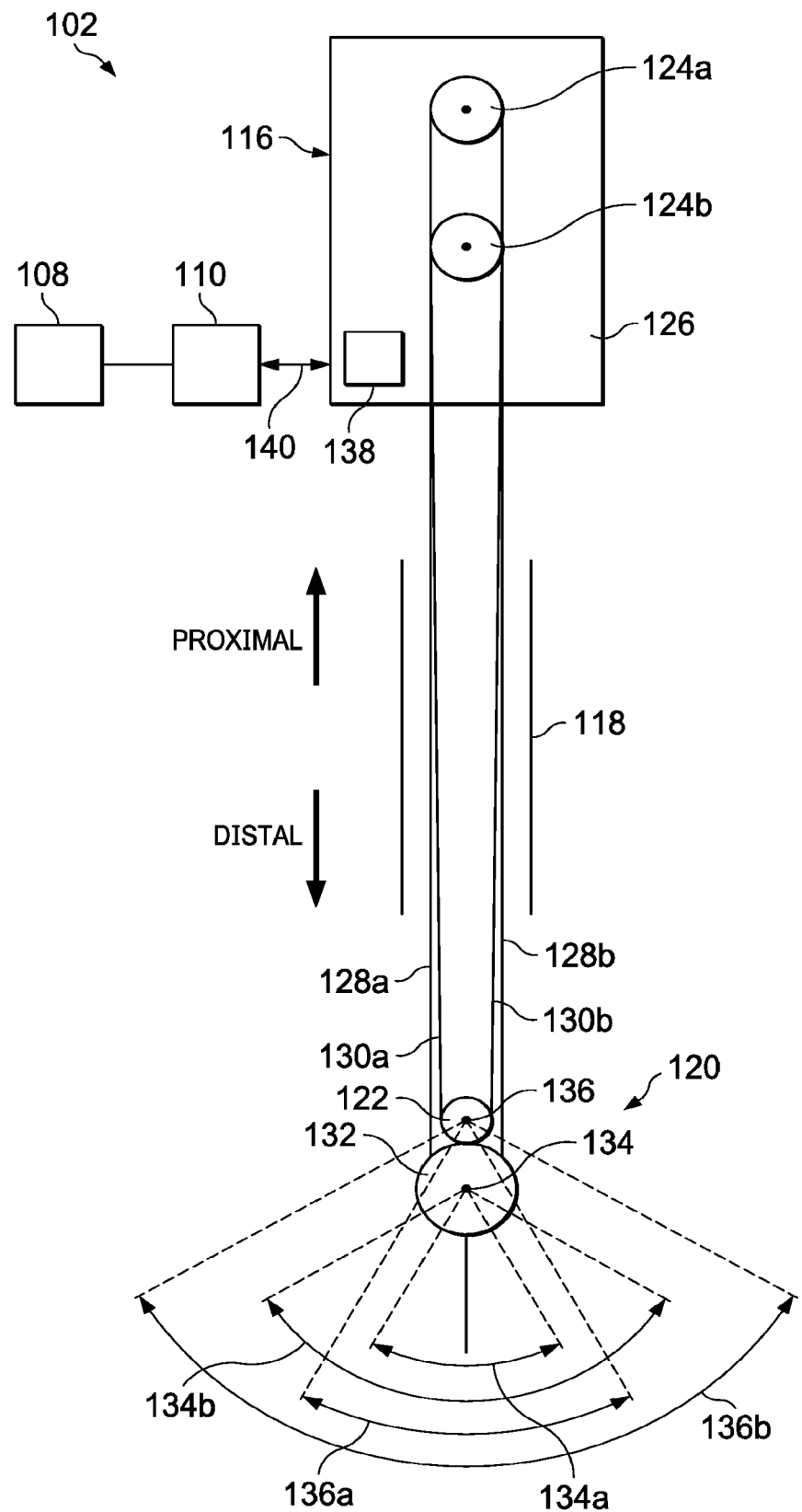
FIG. 2 is a schematic view of an instrument of the telesurgical system and example operating parameter ranges.

Referring to FIG. 2, instrument 102's major components include a proximal end mechanism 116, a hollow instrument shaft 118 coupled at one end to proximal end mechanism 116, a movable surgical end effector 120 coupled to the distal end of instrument shaft 118, and an optional movable wrist mechanism 122 coupled between the distal end of shaft 118 and end effector 120. Proximal (located away from the patient) and distal (located toward the patient) directions are indicated in the figure for clarity. Instrument shaft 118 may be straight or curved or jointed, and the shaft may be rigid or flexible. End effector 120 carries out a therapeutic, diagnostic, or imaging surgical function, or any combination of these functions. Various instrument wrist mechanism configurations are known—see e.g., U.S. Pat. No. 6,394,998 B1 (filed Sep. 17, 1999), U.S. Pat. No. 6,817,974 B2 (filed Jun. 28, 2002), U.S. Pat. No. 9,060,678 B2 (filed Jun. 13, 2007), and U.S. Pat. No. 9,259,275 B2 (filed Nov. 12, 2010), the disclosures of which are incorporated herein by reference.

As shown, proximal end mechanism 116 includes two illustrative rotating cable drive capstans 124a,124b surrounded by a housing 126. A first pair of cables 128a,128b is wrapped around capstan 124a so that one cable pays out and the other cable pays in as capstan 124a rotates, and vice-versa. Similarly, a second pair of cables 130a,130b is wrapped around capstan 124b so that one cable pays out and the other cable pays in as capstan 124b rotates, and vice-versa. The capstans 124a,124b receive drive inputs from instrument drive interface 110 under the control of control system 108, as described previously.

Cables 128a,128b extend through instrument shaft 118 and are coupled to a movable end effector component 132, such as a movable jaw, scissor blade, electrocautery hook or blade, and the like. Accordingly, end effector component 132 moves in correspondence with capstan 124a rotation. Likewise, cables 130a,130b extend through instrument shaft 118 and are coupled to wrist 122 so that wrist 132 moves in correspondence with capstan 124b rotation. Wrist 122 is illustrative of various jointed mechanical wrist configurations, such as nested-clevis and serial link ("snake") configurations of Endowrist® Surgical Instruments commercialized by Intuitive Surgical.

The capstans 124a,124b and their associated drive inputs, cable routing guides or pulleys, bearings, etc. are illustrative of various mechanisms ("transmission mechanisms") that receive a force or torque drive input and transmit the received drive input to corresponding motion used to control a distal instrument component, such as wrist 122 or end effector component 132. Such transmission mechanisms include rotating disk and various other axially rotating inputs; rotating, rack, or worm gear inputs; lever or gimbal inputs; sliding tab and other laterally translating inputs; pin and other axially translating inputs; fluid pressure inputs; and the like. Further, capstans 124a,124b are illustrative of instrument configurations in which one or more motors are mounted within or are coupled to housing 126 and receive motor control input from control system 108 through housing 126. The motor or motors drive a corresponding transmission mechanism. Thus an instrument component may be moved by a motor outside (e.g., in a manipulator to which the instrument is mounted, or mounted to the instrument) or inside the instrument.

The cable pairs 128a,128b and 130a,130b are illustrative of various components ("actuation components") optionally used to transfer force or torque from a transmission mechanism to a distal end component of the instrument. Such actuation components include tension components (e.g., cables, cable-hypotube combinations, pull rods, etc.), compression components (e.g., push rods, Bowdin cables, etc.), rotating components (e.g., shafts, gear trains, etc.), and components that combine these characteristics (e.g., push/pull rods, splined shafts that rotate and translate, etc.).

Additional transmission mechanism and actuation components include rotating shafts, gears, hinges, pivot points, rolling surfaces, rotating or sliding parts, cam surfaces and cam pins, lead screws, universal or constant-velocity joints, load bearing bearings, surfaces, or points, and the like.

Operating Modes

In an inventive aspect, a parameter that affects instrument life is divided into two or more ranges—one range having relatively less affect on instrument life, and the other range (s) having relatively more affect on instrument life. Instrument life is extended by operating the instrument within the parameter range having relatively less affect on instrument life, although the parameter range(s) having relatively more affect on instrument life are available if needed. An example parameter is a mechanical component range of motion ("ROM"). Inventive aspects are generally illustrated by telesurgical system components having two ROMs available for user selection, and it should be understood that aspects include systems having three or more ROMs that are available for user selection. In addition, inventive aspects are illustrated by mechanical ROMs, but persons of skill in the art will understand that other instrument or telesurgical system parameter ranges may be defined and selected, as described below. Thus two, three, or more parameter ranges may be selected.

FIG. 2 illustrates that instrument 102's movable distal end components each have a ROM. And, in accordance with inventive aspects, one or more distal end component ROMs may be selectively varied. Any limited ROM or ROMs within a component's maximum ROM may be defined to be selected by operating in a corresponding operating mode. As shown, for example, end effector component 132 rotates around axis 134 within a first selected ROM 134a (e.g., ±30°) or within a second selected ROM 134b (e.g., ±60°) larger than the first selected ROM. Similarly, wrist 122 rotates around axis 136 within a first selected ROM 136a (e.g., ±30°) or within a second selected ROM 136b (e.g., ±60°) larger than the first selected ROM. The various selected ROMs are optionally symmetric or asymmetric (e.g., ±30°, +0° to −45°, +45° to −15°, +30° to +60°, etc.). And, the first and second ROMs may fully overlap (e.g., a first ROM ±60° and a second ROM ±30° from a reference angle) or partially overlap (e.g., a first ROM +15° to −45° and a second ROM 0° to −60° from a reference angle). The selected ROM will correspond to the type of joint (e.g., a rotational joint has selected rotational ROMs, a prismatic joint has selected translation ROMs, etc.).

The illustrated wrist 122 and end effector component 132 are shown having a single mechanical degree of freedom ("DOF"). But, if a single joint or joint assembly is capable of two or more DOFs that each have an associated ROM, the DOFs and the ROMs associated with the DOFs may be selectively limited in various ways. For example, one selected ROM for such a joint or joint assembly may limit a first DOF ROM but not a second DOF ROM, and a second selected ROM for such a joint or joint assembly may limit both the first DOF ROM and the second DOF ROM. As another example, an instrument wrist mechanism may include two or more single-DOF mechanical joints but is controlled as a single joint having multiple DOFs, and so many selectable wrist mechanism ROMs are possible (e.g., pitch ±45° and yaw ±45°; pitch ±60° and yaw ±60°; pitch +15° to −45° and yaw ±45°, etc.). In some aspects, a selected ROM corresponds to a full mechanical ROM (i.e., mechanical stop-to-stop) for a single mechanical joint.

Further, in telesurgical systems having more than one instrument, a selected ROM may apply to a single instrument or to a group of two or more instruments. For example, in a first telesurgical system operating mode, a first selected ROM corresponds to two or more instruments operating at their full mechanical ROMs, and a second selected ROM corresponds to two or more instruments operating within a limited ROM. Alternately, selectable ROMs are independently available for two or more individual instruments.

In another aspect, two or more ROMs available for selection depend on the specific type of instrument mounted to a manipulator. For example, a first instrument type (e.g., a grasper) may have two selectable operating modes: a first mode in which the first instrument wrist's full pitch and yaw ROMs are available, and a second mode in which the first instrument wrist's pitch and yaw ROMs are limited (e.g., ±45°). A second instrument type (e.g., monopolar cautery shears) may have two different selectable operating modes: a first mode in which the second instrument wrist's full pitch and yaw ROMs are available, and a second mode in which the second instrument wrist's pitch and yaw ROMs are limited (e.g., ±30°). Likewise, a first instrument type may have one quantity (e.g., two) of selectable ROMs available, and a second instrument type may have a different quantity (e.g., three) of selectable ROMs available. And in some aspects, one specific instrument type may not have any selectable ROMs available (i.e., the full instrument ROM(s) are always available), and another specific instrument type has two or more selectable ROMs available.

In accordance with an inventive aspect, these operating modes are used to extend instrument life in a telesurgical system, as described below.

Operating Parameter Ranges

Various operating parameters may be used to describe the environment in which control system 108 commands instrument and instrument component movement. One parameter is position or orientation within a range of motion, as discussed above. Other parameters include component velocities, accelerations, static force or torque applications and loads, and dynamic force or torque applications and loads. Thus various ranges within these parameters may be defined and selected as described above.

Figure 3A:
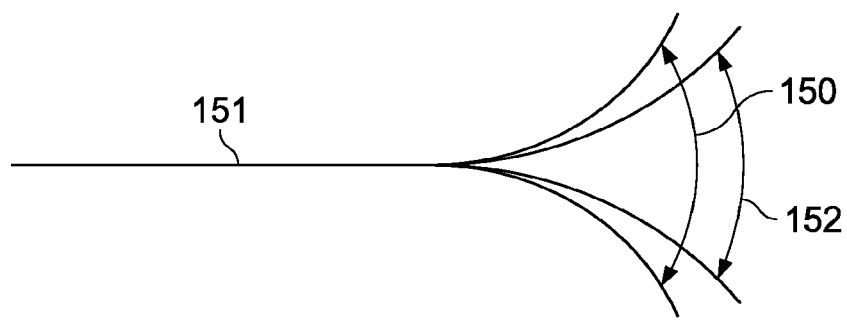
FIGS. 3A-3C are schematic views of instrument components and example associated operating parameter ranges.
Figure 3B:
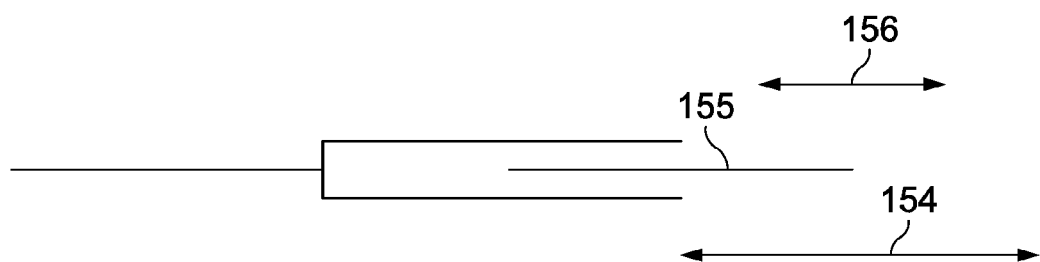
Figure 3C:
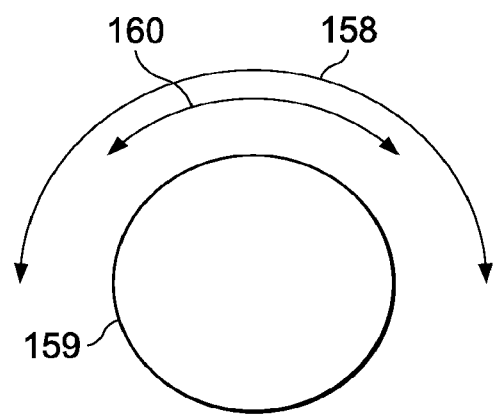

For example, FIGS. 3A-3C illustrate instrument operating parameters. FIG. 3A is a schematic of an instrument 151 having a snake-like distal end (e.g., a catheter, a guide tube, etc.). Double-headed arrow 150 represents a full parameter range associated with movement of a flexible instrument component, such as mechanical ROM, lateral force, distal tip velocity, distal tip acceleration, pull force on an actuation cable, etc. constrained by the physical limits of the instrument and associated actuation components. Double-headed arrow 152 represents a limited parameter range as constrained by the control system.

FIG. 3B is a schematic of an instrument component 155 translating at a prismatic joint (e.g., a push rod, a knife blade, a stapler sled, etc.). Double-headed arrow 154 represents a full parameter range associated with straight or curvilinear translation, such as mechanical ROM, axial push or pull force, component velocity, component acceleration, etc. constrained by the physical limits of the joint, the component, and the associated actuation components. Double-headed arrow 156 represents a limited parameter range as constrained by the control system.

FIG. 3C is a schematic of a cross section of an instrument component 159 (e.g., a rotating drive shaft, a disk, a gear, a hinge pin, etc.). Double-headed arrow 158 represents a full parameter range associated with rotation, such as mechanical ROM, torque, angular velocity, angular acceleration, etc. constrained by the physical limits of the component and the associated actuation components. Double-headed arrow 160 represents a limited parameter range as constrained by the control system.

During operation of the telesurgical system, the value of each of these parameters can be determined within a range, and so the control system may record the amount of time a component spends within a predefined parameter range. Likewise, the control system may record the number of events associated with a parameter range or value.

For example, the control system may record the amount of time a moveable component operates within a parameter range, such as the amount of time a component operates within a 60-90-degree ROM. Or, events such as the number of times the component moves into the 60-90-degree ROM or the number of times the component exceeds 60 degrees may be recorded.

In accordance with an inventive aspect, information about these parameter ranges or events is used to extend instrument life in a telesurgical system, as described below. This information may be combined with information about the selected parameter operating range. Or, it may be used independently of any selected operating parameter range.

Instrument Life

As with all mechanisms, movable instrument components can degrade from use. Therefore, for safety a telesurgical system typically limits the time an instrument may be used. For example, an instrument design is tested to determine expected average maximum life, and then a large safety margin is introduced to define a maximum usable life that is shorter than the expected average maximum life.

The maximum usable life may be defined in various ways, such as by defining maximum instrument allowable discrete uses ("lives") or by defining a maximum instrument allowable time in use. For example, a new individual instrument may be assigned an allowed ten usable discrete lives, and the number of usable discrete lives remaining is stored in memory in the instrument, in the telesurgical system, or at a networked location, so control system 108 can access the stored information. Likewise, a new individual instrument may be assigned an allowed usable time, and the time of allowable use remaining is stored in memory in the instrument, in the telesurgical system, or at a networked location, so control system 108 can access the stored information. Once the maximum instrument allowable discrete uses or the maximum instrument allowable usable time is assigned, the number of discrete uses remaining or the usable time remaining is reduced as the instrument is used during medical treatment.

In one example variation, one usable discrete life is decremented for each surgical procedure (single patient—start to finish) in which the instrument is used until zero usable discrete lives remain, at which time the surgical system prevents further use of the individual instrument.

In another example variation, one usable discrete life is decremented each time the individual instrument is mounted and initialized on a manipulator until zero usable discrete lives remain.

In another example variation, as the instrument is used, the surgical system decrements usable time remaining until zero usable time remaining exists. When zero usable time remains, the surgical system optionally (a) prevents further use of the instrument and signals that a replacement instrument is required; (b) allows use of the instrument to be continued until the instrument is removed from the manipulator and prevents further use of the instrument after the instrument is removed from the manipulator; or (c) allows use of the instrument to be continued during an entire surgical procedure, including one or more removals and one or more later mountings to a manipulator, and then prevents further use of the instrument after the surgical procedure.

Thus the usable life of an instrument begins at a defined initial maximum usable life, and the usable life of the instrument is reduced as the instrument is used until zero usable life remains for the instrument. Usable life of an instrument is illustrated in this description by discrete lives remaining or time of use remaining, but other measures of usable life may be applied, such as instrument performance measurement (e.g., sensed actual component position in relation to commanded component position, sensed electrosurgical energy, sensed torque for surgical staple formation, etc.) as a dynamic indication of usable life remaining.

The usable life of an individual instrument, such as allowable discrete lives or time of use remaining, may optionally be stored in the instrument itself, in the telesurgical system, or at a network location with which the telesurgical system communicates. And, updates to the usable life may optionally be made at various times. For example, time remaining may be continuously updated while the instrument is in use, or the control system may record the total time the instrument is used and update the usable time remaining when the instrument is withdrawn from the patient. Similarly, the usable discrete lives remaining may be decremented while the instrument is in use, or the control system may determine the discrete lives used and update the discrete lives remaining when the instrument is withdrawn. As another example, the time or discrete lives used may be recorded for an instrument for the time the instrument is mounted to a manipulator, and then the time or lives remaining is updated when the instrument is again coupled to a manipulator.

Referring again to FIG. 2, in one aspect surgical instrument 102 includes a memory 138, which in some embodiments includes stored information such as instrument type, a serial number unique to the instrument, usable life remaining (e.g., number of allowable discrete lives or allowable time remaining), etc. This information stored in memory 138 is communicated 140 via drive interface 110 to control system 108. Optionally, information such as updated allowable discrete lives or time remaining is communicated 140 from control system 108 via drive interface 110 to memory 138 so that the information can be accessed the next time the instrument is used in the teleoperated surgical system. An example of instrument memory and communication via a drive interface is found in U.S. Pat. No. 6,331,181 B1 (filed Oct. 15, 1999), which is incorporated herein by reference. Likewise, the instrument discrete life or time information may be stored at a network location accessed by control system 108 of the telesurgical system.

The amount of degradation of an instrument's capability in many situations varies depending on the operating parameter range in which the instrument is used. For example, as an instrument component moves within its associated DOF ROM, more mechanical degradation may be expected in the component at the extremes of the ROM than near the center of the ROM. More specifically, a cable used to move an end effector jaw may experience relatively less degradation over time as the cable is routed around one or more pulleys or guide surfaces to move the jaw ±30 degrees from a defined center position (e.g., the instrument's longitudinal axis between proximal and distal ends), and the cable may experience relatively more degradation over time as the cable is routed around the one or more pulleys or guide surfaces to move the jaw ±60 degrees from the defined center position, and the cable may experience relatively even more degradation over time as the cable is routed around the one or more pulleys or guide surfaces to move the jaw ±90 degrees from the defined center position.

Further, the amount of degradation may not be a linear function of the parameter value within a range of parameter values. For example, transmission mechanism component or actuation component degradation may not be a linear function of the associated distal end component's ROM location. As a more specific example, component degradation for end effector jaw movement near the jaw's maximum ROM (e.g., near 90 degrees) may be significantly higher (e.g., more than 3×) than for jaw movement near the defined center position or within a limited ROM (e.g., ±30 degrees), although 90 is three times 30.

In addition, a movable component may degrade relatively more quickly as its velocity or acceleration increases. For example, a component may experience relatively higher degradation over time if its velocity is limited only by the component's maximum possible actuated velocity, and it may experience relatively lower degradation over time if its velocity is limited to a value less than the component's maximum possible actuated velocity. Similarly, a component may experience relatively higher degradation over time if its acceleration is limited only by the component's maximum possible actuated acceleration, and it may experience relatively lower degradation over time if its acceleration is limited to a value less than the component's maximum possible acceleration.

Further, a movable transmission mechanism component or actuation component may degrade relatively more quickly as a static force or torque load, dynamic mechanical actuation force or torque load, or a combined static load and dynamic actuation load on the part increases. For example, a component may experience relatively higher degradation over time if its maximum permitted actuation load is the maximum possible actuation load (e.g., to cause maximum grip force, maximum bending force, or maximum torque on a component; working near or in a component's range of elastic deformation) and relatively lower degradation over time if its maximum permitted actuation load is less than the maximum possible actuation load. Load may be directly measured (e.g., by using a force or torque sensor coupled to the component) or indirectly measured (e.g., by sensing motor current in the motor used to move the component or to hold it in place under load, and then inferring load from the motor current used).

Similarly, in an instrument in which a constantly present preload force or torque is on a component (e.g., a cable), the component may experience relatively higher degradation over time if its preload force or torque is at a first value as actuation force or torque is applied, and may experience relatively lower degradation over time if its preload force or torque is at a second value, less than the first value, as actuation force or torque is applied. An example of such preload force is a constant preload tension force on actuation cables in an instrument in order to keep the cables from going slack or leaving their defined paths. Another example of a preload force is the force experienced in a transmission mechanism or actuation component that is used to eliminate lost motion caused by gaps (backlash) in an antagonistic control pair in which one of the pair moves an instrument component in one direction (e.g., pitch/heave up, yaw/sway left, roll clockwise, surge proximally) and the other drivetrain of the pair moves the instrument component in the opposite direction (e.g., pitch/heave down, yaw/sway right, roll counterclockwise, surge distally). Thus a component may experience relatively higher degradation over time with a combination of relatively higher preload force and an actuation force, and a relatively lower degradation over time with a combination of a relatively lower preload force and the same actuation force. In addition, a long-term static load alone may result in mechanical degradation, such as cable stretch under high preload tension for many months. The amount of time between when an instrument was built (e.g., when the static preload force is first applied) and the time the instrument is used may be relevant to instrument performance.

Determining Instrument Life

In one aspect the control system records the amount of time spent in each of two or more operating modes in which a parameter is differently limited, and then these times are used to determine usable instrument life remaining. For example, the control system records the time spent in a first selected mode in which a ROM is limited and the time spent in a second selected mode in which the ROM is unlimited.

In another aspect the control system records the amount of time spent in two or more parameter ranges, and then these times are used to determine usable instrument life remaining. For example, the control system records the time spent within a first predefined mechanical ROM (e.g., 0-30 degrees) and the time spent in a second predefined mechanical ROM beyond the first predefined mechanical ROM (e.g., 30-60 degrees).

In another aspect, the time spent in each of two or more operating modes and time spent in one or more parameter ranges are combined to determine usable instrument time remaining. For example, the control system records the time spent in a first selected mode in which a ROM is limited (e.g., 0-45 degrees) and the time spent in a second selected mode in which the ROM is unlimited (e.g., 0-90 degrees), and it also records the amount of time spent in a predefined ROM (e.g., 70-90 degrees). The control system may then use this combined information to determine the instrument's usable life remaining.

Again, although mechanical ROMs are used as example parameters, they are representative of any parameter that affects mechanical degradation over time and that can be monitored or changed from one value to a second value, or from one range of values to another range of values, and that correspondingly changes the mechanical degradation over time. In addition, although the examples above are individual parameters such as ROM, velocity, acceleration, actuation force or torque, and preload force or torque, two or more of these parameters may be limited to further reduce instrument component degradation over time. Thus the term "selected parameter range" includes a range of a single parameter and ranges of two or more parameters.

As mentioned above, in some instances the degradation of an individual component depends on two or more parameter values. For example, if a Carden joint is at a zero bend angle, then the Carden joint's degradation over time may be mainly caused by its maximum permitted velocity or actuation load. But if the Carden joint is at a high bend angle (e.g., 60 degrees), then in a combination of this bend angle with maximum permitted angular velocity or actuation load, or in a combination of this bend angle with maximum permitted angular velocity and actuation load, the bend angle may become the dominant parameter in the joint's degradation over time. Thus a parameter associated with instrument component degradation over time may have a single dimension or may have two, three, or more dimensions. And, the value of one parameter or one dimension of a parameter may determine a second parameter's or a second dimension's effect on degradation over time of a component.

Often, one or more instrument components degrade over time sooner than others, and so these one or more instrument components determine the expected average maximum life of an instrument type and consequently the defined maximum usable life for the instrument type. Limiting degradation over time of these one or more components increases the expected average maximum life of the instrument type and the associated defined maximum usable life of the instrument type.

Therefore in one aspect, maximum usable instrument life is extended in a mode that limits range of one or more instrument operating parameters (such as range of motion) for one or more movable instrument components, as compared to maximum usable instrument life in a mode that does not limit the range of the instrument operating parameter. The telesurgical system's computer control unit determines the extended allowable discrete lives or time as a function of the limited operating parameter (e.g., the time spent in the limited parameter operating mode), adjusts the instrument's remaining allowable lives or time, and stores the adjusted allowable remaining discrete lives or time for access in one or more subsequent surgical procedures.

The allowable discrete lives remaining may optionally be decremented in fractions of discrete lives, so that operating in a mode that limits an instrument operating parameter for two or more procedures is required to extend allowable discrete instrument lives remaining by a full discrete life.

For example, as a result of a first surgical procedure in which a limited parameter range is selected, the allowable discrete instrument lives remaining is decremented by one-half. And, as a result of a second surgical procedure in which the limited parameter range is selected, the allowable discrete instrument lives remaining is decremented by another one-half. Therefore, after the first and second surgical procedures, the allowable discrete instrument lives remaining is extended by a full discrete instrument life, because instead of two discrete lives decremented (one per each procedure), only a single discrete life is decremented after the two procedures. The telesurgical system determines the number of full discrete instrument lives remaining and so allows the additional full discrete instrument life to be used for a subsequent surgical procedure.

Time spent in an operating mode may optionally be correlated to extending allowable remaining discrete instrument lives or time. For example, during a first surgical procedure a limited operating parameter range is selected for one half the time the instrument is used, and so the allowable discrete instrument lives remaining is decremented by three-quarters. Then, during a second surgical procedure the limited operating parameter range is selected for the full procedure, and so the allowable discrete instrument lives remaining is decremented by one-half. And, during a third surgical procedure the limited operating parameter range is selected for three-quarters of the procedure, and so the allowable discrete instrument lives remaining is decremented by five-eighths. Therefore, after these three procedures the total discrete lives have been decremented by less than two, and so an additional discrete instrument life is available. As another example, during a first surgical procedure a limited operating parameter range is selected for one-half the time the instrument is used, and so usable time remaining is decremented by three-quarters of the full time the instrument is used. The correlations in these examples are arbitrarily selected as illustrations. In practice, the correlations are worked out based on actual instrument lifecycle testing, which may vary from instrument type to instrument type, and may vary based on parameter ranges chosen.

In another aspect, maximum usable instrument life is extended by the control system sensing and recording occurrences or time spent in which one or more movable instrument components operate in one or more operating parameters (such as range of motion), adjusting the instrument's remaining allowable discrete lives or time, and storing the adjusted remaining lives or time for access in one or more subsequent surgical procedures. The adjusting may be done in a way similar to the way the adjusting is done when operating modes are discretely selected.

In another aspect, parameter ranges may be associated with usable instrument life remaining. The instrument optionally defaults to a full parameter range during an early portion of instrument life remaining, and then defaults to a limited parameter range during a later portion of instrument life remaining, with the full parameter range or an increased parameter range available when needed. For example, for an instrument with a mechanical DOF having a ±90° ROM, a ±60° ROM may be available as a default when the instrument is first used, and the surgeon may select the full ±90° ROM when needed. As usable instrument life is consumed past a certain value, however, the default ROM changes to ±45° ROM, and the surgeon may select the full ±90° ROM when needed. As a further example, as usable instrument life is consumed past a certain value, the default ROM changes to ±45° ROM, and ±60° and ±90° ROMs are made available for selection when needed. As another example, as usable instrument life is consumed past a certain value, the default ROM changes to ±45° ROM, and the surgeon may select a less limed ±60° ROM when needed, but the full ±90° ROM is not available for selection. In this situation, if the full parameter range is needed, an instrument having the unconstrained full parameter range must be used.

In a variation of this aspect, parameter ranges are associated with usable instrument life remaining without having two or more selectable parameter ranges. As usable instrument life is consumed, the parameter range is correspondingly limited. For example, during an early portion of usable instrument life, a full parameter range is available, and during a later portion of usable instrument life, only a limited parameter range is available. Again, if the full parameter range is needed, an instrument having the unconstrained full parameter range must be used.

Selecting an Operating Mode

Referring once again to FIG. 1, in one aspect a surgeon selects one of two or more instrument operating parameter limits as described above by entering a selection via operating mode input 114 on a surgeon control unit. Generally, in one operating mode the full parameter range is available to the surgeon if clinically required. The parameter range is limited in the second operating mode. The telesurgical system may optionally operate in various other operating modes (third, fourth, fifth, etc.) that either further limit one parameter's range, limit one or more additional parameter ranges, or both.

In one aspect, a teleoperated surgical system defaults to a first operating mode in which an instrument operating parameter range is limited to a first range, and the surgeon may select a second operating mode in which the instrument operating parameter range is limited to a second range that is either larger than the first range or not limited. For example, the teleoperated surgical system is initialized in a first operating mode in which instrument wrist pitch and yaw ROMs are limited to ±45°, and the surgeon may then select a second operating mode in which the instrument pitch and yaw ROMs are unlimited or limited to at or near the full possible physical ROMs. A limited range default may occur upon system start-up, upon instrument installation, upon reestablishing the master-slave relationship after an interruption, upon sensing operation within the limited range for a predetermined time, or upon any other relevant system event.

In one aspect, a teleoperated surgical system defaults to a first operating mode in which an instrument operating parameter range is not limited or is limited to near the parameter's full range, and the surgeon may select a second operating mode in which the instrument operating parameter range is limited. For example, the teleoperated surgical system is initialized with instrument wrist pitch and yaw ROMs are unlimited or limited to at or near the full possible physical ROMs, and the surgeon may then select a second operating mode in which the instrument pitch and yaw ROMs are limited to ±45°. An unlimited range default may occur upon system start-up, upon instrument installation, upon establishing the master-slave relationship after an interruption, upon sensing a predetermined number of times within a predetermined time period that a master haptic limit for the parameter is reached, or upon any other relevant system event.

In one aspect, when a telesurgical system is operating in a mode in which an instrument operating parameter is limited, the telesurgical system's computer control system limits a corresponding master input parameter to help the surgeon understand that the parameter is limited. For example, in a telesurgical system operating mode in which a movable instrument component ROM is limited, the corresponding master ROM is limited. If a first operating mode limits the instrument ROM component to ±45°, the control system places a haptic limit on the master that limits the corresponding master DOF to ±45°. This allows the surgeon to sense the limited ROM, and then to select the second operating mode in which the ROM is unlimited if additional instrument component ROM is desired. As described above, the surgeon may select the second operating mode in various ways, such as by a discrete selection on the master or on the surgeon control unit, by moving through a haptic sensory cue (e.g., a haptic "wall"), or by any other suitable control input (e.g., foot pedal, voice, eye gaze menu selection, etc.).

In one aspect, the control system automatically selects an operating mode associated with a limited parameter range after a movable mechanical component has operated within the limited parameter range for a predetermined amount of time. For example, the control system may initially select a first, limited parameter range (e.g., ±60° ROM) operating mode when an instrument is first installed. Then, a surgeon selects and uses a second, unlimited parameter range (e.g., ±90° ROM) operating mode because of a clinical requirement. As the surgeon continues to work for a defined time, the control system determines that the surgeon is no longer using the unlimited parameter range, and so the control system once again selects the first, limited parameter range to prevent the surgeon from inadvertently operating in the second parameter range that results in increased component mechanical degradation. The surgeon may once again select the second operating mode if necessary.

What is claimed is:

1. A telesurgical system comprising:
a teleoperated manipulator; and
a control system to execute instructions to perform operations comprising:
  determining a remaining usable life value of a surgical instrument before a use of the surgical instrument mounted to the teleoperated manipulator, the surgical instrument comprising a distal end component and an actuation component coupled to move the distal end component when driven by the teleoperated manipulator,
  monitoring an amount of use of the actuation component during a use of the surgical instrument while mounted to the teleoperated manipulator, wherein monitoring the amount of use of the actuation component comprises determining the amount of use of the actuation component based on a force or torque on the actuation component, and
  updating the remaining usable life value to an updated usable life value of the surgical instrument based at least on the amount of use of the actuation component during the use of the surgical instrument.

2. The telesurgical system of claim 1, wherein:
updating the remaining usable life value comprises one of:
updating the remaining usable life value to a first remaining usable life value based on a first amount of use of the actuation component during the use of the surgical instrument, or
updating the remaining usable life value to a second remaining usable life value based on a second amount of use of the actuation component during the use of the surgical instrument;
the second amount of use of the actuation component is different from the first amount of use; and
the second remaining usable life value is different from the first remaining usable life value.

3. The telesurgical system of claim 1, wherein:
the operations further comprise preventing further use of the surgical instrument based on the updated remaining usable life value of the surgical instrument.

4. The telesurgical system of claim 3, wherein:
the use of the surgical instrument occurs during a first surgical procedure; and
preventing further use of the surgical instrument based on the updated remaining usable life value of the surgical instrument comprises preventing the further use of the surgical instrument during a second surgical procedure subsequent to the first surgical procedure.

5. The telesurgical system of claim 1, wherein:
the operations further comprise generating a signal indicating a replacement surgical instrument is required based on at least the updated usable life value of the surgical instrument.

6. The telesurgical system of claim 1, wherein:
monitoring the amount of use of the actuation component comprises determining the amount of use of the actuation component based on at least one of a static force on the actuation component, a static torque on the actuation component, a dynamic force on the actuation component, or a dynamic torque on the actuation component.

7. The telesurgical system of claim 6, wherein:
monitoring the amount of use of the actuation component comprises measuring a current of a motor used to drive the actuation component, the current of the motor being indicative of the static force, the static torque, the dynamic force, or the dynamic torque.

8. The telesurgical system of claim 1, wherein:
monitoring the amount of use of the actuation component comprises determining the amount of use of the actuation component based on at least one of a preload force on the actuation component or a preload torque on the actuation component.

9. The telesurgical system of claim 1, wherein:
monitoring the amount of use of the actuation component comprises determining the amount of use of the actuation component based on at least one of an acceleration of the actuation component or a velocity of the actuation component.

10. The telesurgical system of claim 1, wherein:
monitoring the amount of use of the actuation component comprises determining the amount of use of the actuation component based on at least an amount of stretch of the actuation component.

11. The telesurgical system of claim 1, wherein:
monitoring the amount of use of the actuation component comprises determining the amount of use of the actuation component based on at least a bend angle of the actuation component.

12. The telesurgical system of claim 1, wherein:
monitoring the amount of use of the actuation component of the surgical instrument during use of the surgical instrument comprises monitoring an amount of degradation of the actuation component.

13. The telesurgical system of claim 1, wherein:
the actuation component comprises an actuation cable; and
monitoring the amount of use of the actuation component comprises monitoring the amount of use of the actuation cable based on at least a routing path of the actuation cable.

14. The telesurgical system of claim 1, wherein:
updating the remaining usable life value comprises updating the remaining usable life value at least based on a number of surgical procedures in which the surgical instrument is used.

15. A medical device comprising:
a surgical instrument comprising a distal end component and an actuation component coupled to move the distal end component; and
a control system configured to execute instructions to perform operations comprising:
  determining a remaining usable life value of the surgical instrument before a use of the surgical instrument,
  monitoring an amount of use of the actuation component during the use of the surgical instrument, wherein monitoring the amount of use of the actuation component comprises determining the amount of use of the actuation component based on a force or torque on the actuation component, and
  updating the remaining usable life value to an updated usable life value of the surgical instrument based at least on the amount of use of the actuation component during the use of the surgical instrument.

16. The medical device of claim 15, wherein:
updating the remaining usable life value comprises one of:
updating the remaining usable life value to a first remaining usable life value based on a first amount of use of the actuation component during the use of the surgical instrument, or updating the remaining usable life value to a second remaining usable life value based on a second amount of use of the actuation component during the use of the surgical instrument;
the second amount of use of the actuation component is different from the first amount of use; and
the second remaining usable life value is different from the first remaining usable life value.

17. The medical device of claim 15, wherein:
the operations further comprise preventing further use of the surgical instrument based on the updated remaining usable life value of the surgical instrument.

18. The medical device of claim 17, wherein:
the use of the surgical instrument occurs during a first surgical procedure; and
preventing further use of the surgical instrument based on the updated remaining usable life value of the surgical instrument comprises preventing the further use of the surgical instrument during a second surgical procedure subsequent to the first surgical procedure.

19. The medical device of claim 15, wherein:
the operations further comprise generating a signal indicating a replacement surgical instrument is required based on at least the updated usable life value of the surgical instrument.

20. The medical device of claim 15, wherein:
monitoring the amount of use of the actuation component comprises determining the amount of use of the actuation component based on at least one of a static force on the actuation component, a static torque on the actuation component, a dynamic force on the actuation component, or a dynamic torque on the actuation component.

21. The medical device of claim 20, wherein:
monitoring the amount of use of the actuation component comprises measuring a current of a motor used to drive the actuation component, the current of the motor being indicative of the static force, the static torque, the dynamic force, or the dynamic torque.

22. The medical device of claim 15, wherein:
monitoring the amount of use of the actuation component comprises determining the amount of use of the actuation component based on at least one of a preload force on the actuation component or a preload torque on the actuation component.

23. The medical device of claim 15, wherein:
monitoring the amount of use of the actuation component comprises determining the amount of use of the actuation component based on at least one of an acceleration of the actuation component or a velocity of the actuation component.

24. The medical device of claim 15, wherein:
monitoring the amount of use of the actuation component comprises determining the amount of use of the actuation component based on at least an amount of stretch of the actuation component.

25. The medical device of claim 15, wherein:
monitoring the amount of use of the actuation component comprises determining the amount of use of the actuation component based on at least a bend angle of the actuation component.

26. The medical device of claim 15, wherein:
monitoring the amount of use of the actuation component of the surgical instrument during use of the surgical instrument comprises monitoring an amount of degradation of the actuation component.

27. The medical device of claim 15, wherein:
the actuation component comprises an actuation cable; and
monitoring the amount of use of the actuation component comprises monitoring the amount of use of the actuation cable based on at least a routing path of the actuation cable.

28. The medical device of claim 15, wherein:
updating the remaining usable life value comprises updating the remaining usable life value at least based on a number of surgical procedures in which the surgical instrument is used.

* * * * *